United States Patent [19]

Obdeijn

[11] Patent Number: 5,030,823

[45] Date of Patent: Jul. 9, 1991

[54] DEVICE FOR INSPECTING THE INNER WALL OF A BODY

[75] Inventor: Marcellines J. J. Obdeijn, Lettele, Netherlands

[73] Assignee: Heuft-Qualiplus B.V., Deventer, Netherlands

[21] Appl. No.: 439,425

[22] Filed: Nov. 20, 1989

[30] Foreign Application Priority Data

Nov. 28, 1988 [NL] Netherlands .......................... 8802933

[51] Int. Cl.$^5$ .............................................. G01N 9/04
[52] U.S. Cl. .................................. 250/223 B; 356/237
[58] Field of Search ........................ 250/223 B, 223 R; 356/237, 240, 428, 445, 241; 209/526, 524; 358/106

[56] References Cited

U.S. PATENT DOCUMENTS 3,150,266  9/1964  Mathias ................................ 250/224
3,761,186  9/1973  Wason ................................. 356/241
4,283,145  8/1981  Miyazawa ........................... 356/240
4,284,353  8/1981  Yoshida et al. .................. 250/223 B
4,500,203  2/1985  Bieringer ......................... 250/223 B
4,758,084  7/1988  Tokumi et al. ..................... 356/240

Primary Examiner—David C. Nelms
Attorney, Agent, or Firm—Willian Brinks Olds Hofer Gilson & Lione

[57] ABSTRACT

A device is provided for inspecting the inner surface of a hollow body, such as a metal container with a cylindrical standing wall and a bottom. Initially, the hollow body and a light source are placed at chosen positions relative to each other, such that the light source can light the inner surface approximately uniformly. A video camera for inspecting the inner surface is positioned such that the direction of lighting and the direction of inspection of each portion of the inner surface approximately coincide.

12 Claims, 2 Drawing Sheets

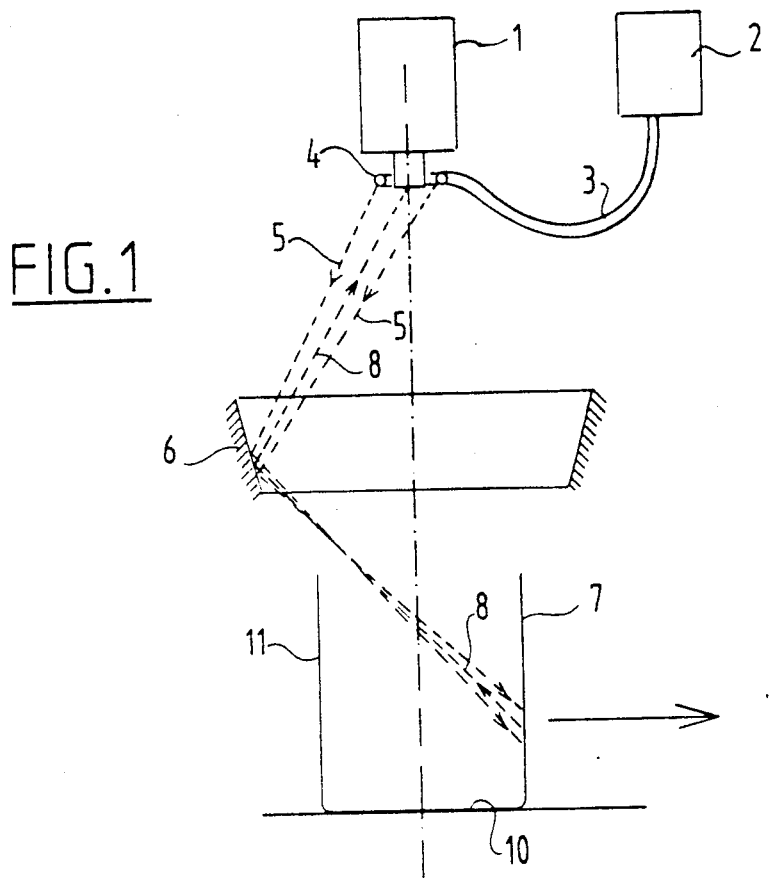
FIG.1
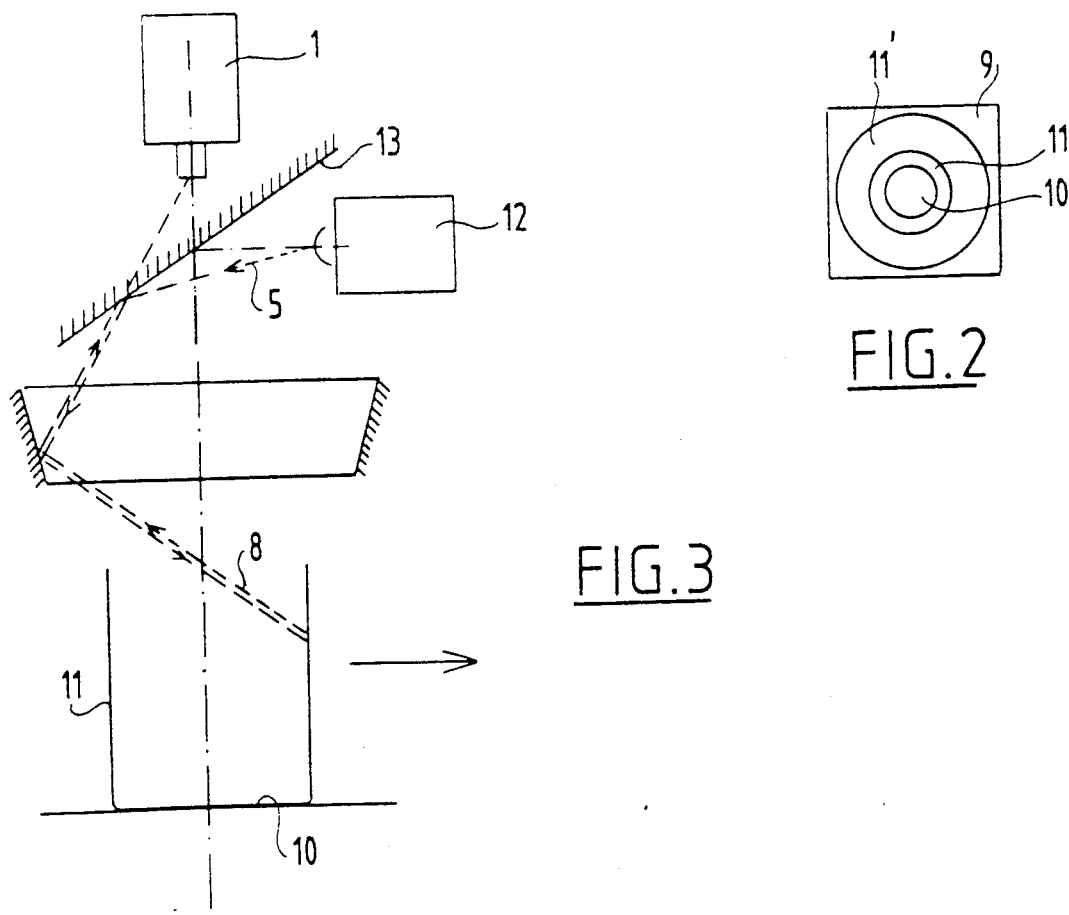
FIG.2
FIG.3

DEVICE FOR INSPECTING THE INNER WALL OF A BODY

BACKGROUND OF THE INVENTION

The invention relates to the inspection of the inside of a body, for example the inner surface of a metal container such as a preserves can.

For the inspection of the bottom of such a can a video camera can be placed above the can for inspection and the interior of the can may be lighted more or less diffusely by means of a continuously or stroboscopically operating light source.

For the standing inner wall of a preserves can such a method of inspection is sometimes less suitable. The purpose of the invention is to cause the inspection to be performed such that detection of faults can take place with the greatest possible reliability and with simple means.

SUMMARY OF THE INVENTION

The best possible inspection is ensured with lighting from the same direction as that from which the inspection, for example with a video camera, takes place. The invention therefore provides a device for inspecting the inner surface of a hollow body such as a metal container with a cylindrical standing wall and a bottom, which device comprises:
- positioning means for placing the body at a chosen position;
- a light source which is placed relative to the positioning means such that it can light the said inner surface at least approximately uniformly; and
- an inspection means, for example a video camera, which is placed relative to the positioning means such that it can inspect the said inner surface, whereby the direction of lighting and the direction of inspection of each portion of the said inner surface at least approximately coincide.

The device can for example display the feature that the light source is at any rate approximately annular and is disposed around the inspection means. Use can be made of a number of light-emitting diodes which are disposed around the objective lens of a video camera or also of a single light source which is connected by means of light conductors to a crown disposed around the said lens and in which the light conductors end. An annular light source is hereby obtained. Use can also be made of a semi-transparent mirror arranged such that the (virtual) images of the light source and the inspection means substantially coincide.

In order to be able to inspect the standing inner surface of, for example, a cylindrical container with the greatest possible resolving power and thereby with the greatest possible detection accuracy, use can be made of a mirror formed, for example in frusto-conical form, such that the inspection means can inspect the inner surface of the body with enlarged angle of aperture. In a particular embodiment the device displays the feature that the mirror has dimensions such that via the mirror only lighting and inspection of the standing wall of the inner surface can take place and that lighting and inspection of the bottom of the inner surface is directly performed.

Attention is drawn to the fact that, depending on the form of a body for inspection and the eventual requirement of a user to be able to inspect a determined portion of the inner surface with greater detection accuracy, use can be made of a mirror with adapted curvature.

A particular embodiment of the invention can be characterized by at least three inspection means each with a light source added thereto, which inspection means together can observe the total inner surface for inspection. The said at least three light sources can be embodied as a single light source which, whether by means of light conductors or with mirrors, causes the lighting of each portion of the inner surface to take place from substantially the same direction as that in which the optical axis extends of each inspection means, in particular video camera.

THE BRIEF DESCRIPTION OF THE FIGURES

The invention will now be elucidated with reference to several embodiments. In the drawing:

FIG. 1 shows a schematically represented first embodiment;

FIG. 2 shows a schematic video image obtained with the disposition according to FIG. 1;

FIG. 3 shows another embodiment;

THE DETAILED DESCRIPTION OF THE PREFERRED EMBODIMENTS

Figure 4:
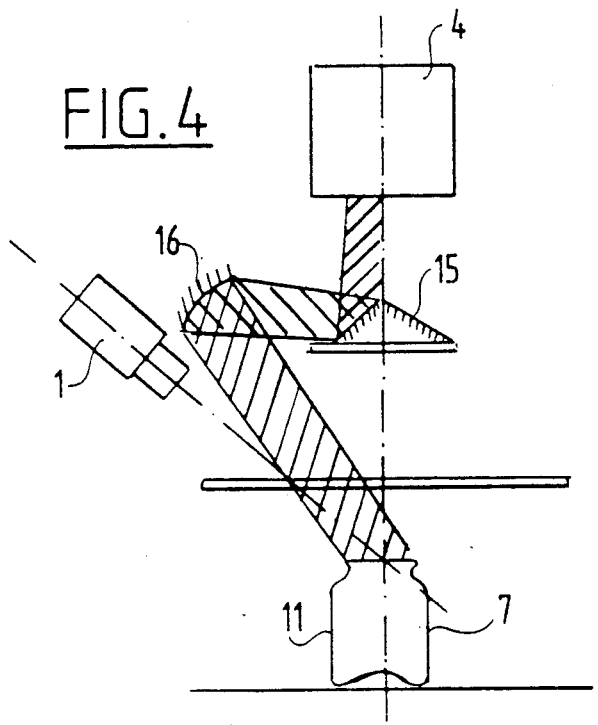
FIG. 4 is yet another embodiment in schematic vertical view.

FIG. 1 shows a video camera 1 and a light source 2 which gives off light by means of an optical conductor 3 via an end crown 4 of the light conductors. The light 5 coming from these light conductors 4 is radiated into a container 7 via a conical mirror 6. The light 8 coming from the lighted zone can be observed from approximately the same direction by the video camera 1. The drawn rays 5, 8 indicate one lighting and inspection zone only by way of example.

FIG. 2 shows a video image 9. The video camera 1 "sees" the bottom of the can directly, as well as the standing inner wall 11. The video camera 1 further inspects the inner wall 11 via the conical mirror 6. This image zone is designated in FIG. 2 by 11'. It will be apparent that the use of the conical mirror 6 achieves as it were an optical enlargement of the standing wall whereby the resolving power of the optical system is better utilized. This is to the benefit of the detection sensitivity.

By making use of a curved mirror instead of the conical mirror 6 a still further effective enlargement can be achieved.

FIG. 3 shows a disposition wherein a light source 12 lights the inner surface 11 of the can 7 via a semi-transparent mirror 13. The light source 12 is placed in relation to the video camera 1 and the semi-transparent mirror 13 such that the optical centre point of the lens system of the camera 1 coincides with the effective location of the light source of the lamp 12.

FIG. 4 shows an arrangement wherein a stroboscopic lamp 14 lights the inside 11 of the can 7 via a three-sided pyramid 15 via a concave mirror 16. The video camera 1 is disposed relative to the mirror 16 such that here too the lighting direction and the inspecting direction of the video camera at least approximately coincide.

Figure 5:
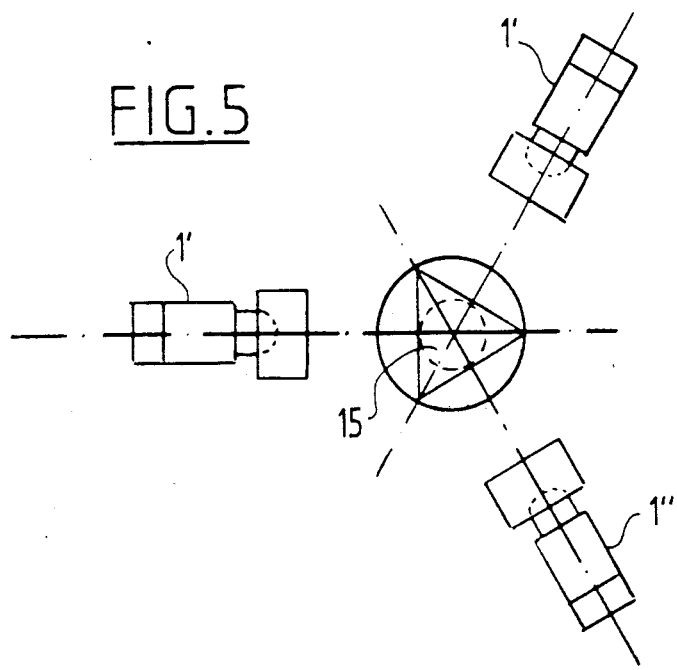
FIG. 5 is a schematic top view of the disposition according to FIG. 4.

FIG. 5 shows a top view from which can be seen that three video cameras 1, 1' and 1" are present, whereby the total inner surface 11 of the can 7 can be inspected at once. It is apparent that the embodiments according to FIGS. 1 and 3 can inspect the entire inner surface with only one video camera, while the arrangement according to FIGS. 4 and 5 needs three cameras therefor. It is however noted that the resolving power of the arrangement according to FIGS. 4 and 5 can be correspondingly greater. The one or the other arrangement may be preferred, depending on the desired sensitivity of detection.

It is generally noted that the form of the mirrors used can be chosen with a view to the desired result.

The use of the semi-transparent mirror according to FIG. 3 can have the drawback that the quantity of light available is effectively reduced. As compensation use could be made for example of a stronger light source.

I claim:

1. The device for inspecting the inner surface of a container, comprising:
   means for generating light connected to an optical conductor, the optical conductor having a substantially circular end crown for projecting light into an open end of the container path;
   means for positioning the container in the path of the light;
   means for aiming the light through an open end of the container and along a first path toward the inner surface of the container, at least some of the light being reflected from the inner surface of the container along a second path to create an image, the second path being substantially coincident with the first path; and
   means for monitoring the image created by the reflected light, the monitoring means being positioned in the second path.

2. The device of claim 1 wherein the optical conductor is at least approximately annular and is disposed around the inspection means.

3. The device of claim 1 wherein the means for aiming the light toward the inner surface of the container comprises a mirror positioned between the means for generating light and the inner surface of the container.

4. The device of claim 1 wherein the monitoring means comprises a video camera.

5. The device of claim 2 wherein the means for aiming the light toward the inner surface of the container comprises a curved mirror positioned between the end crown of the optical conductor and the open end of the container.

6. The device of claim 2 wherein the means for aiming the light toward the inner surface of the container comprises a frusto-conical mirror positioned between the end crown of the optical conductor and the open end of the container.

7. The device of claim 2 wherein the means for monitoring the image created by the reflected light comprises a video camera having a substantially cylindrical receiving portion or receiving reflected light, the video camera conductor is substantially concentric with the receiving portion of the video camera.

8. The device of claim 6 wherein the frusto-conical mirror, the end crown of the optical conductor and the container are positioned substantially concentric with each other such that light is aimed indirectly from the end crown to side surfaces of the container via the mirror and directly from the end crown to a bottom surface of the container.

9. The device of claim 4 wherein the means for aiming the light comprises a semi-transparent mirror and wherein the mean for generating light, the video camera, and the semi-transparent mirror are positioned such that the path of light from the light generating means substantially coincides with the path of the light reflected from the inner surface of the container, at locations between the semi-transparent mirror and the inner surface of the container.

10. The device of claim 1 wherein the means for generating light comprises at least three light sources positioned at spaced locations in the vicinity of the open end of the container.

11. The device of claim 10 wherein the means for monitoring the image created by the reflected light comprises at least three video cameras, each video camera being associated with a respective light source to monitor light originally generated by said respective light source which is reflected from the inner surface of the container.

12. The device of claim 1 wherein the means for generating light comprises a stroboscopic light.

* * * * *

UNITED STATES PATENT AND TRADEMARK OFFICE
CERTIFICATE OF CORRECTION

PATENT NO. : 5,030,823
DATED      : July 9, 1991
INVENTOR(S): Marcellines J.J. Obdeijn It is certified that error appears in the above-identified patent and that said Letters Patent is hereby corrected as shown below:

IN THE CLAIMS

In claim 7, line 4, before "receiving" please delete "or" and substitute therefor --for--.

In claim 9, line 3, before "for" please delete "mean" and substitute therefor --means--.

Signed and Sealed this

Ninth Day of February, 1993

Attest:

STEPHEN G. KUNIN

Attesting Officer     Acting Commissioner of Patents and Trademarks